United States Patent [19]

Sievers

[11] 4,206,132
[45] Jun. 3, 1980

[54] LANTHANIDE CHELATE OF A FLUORINATED LIGAND

[75] Inventor: Robert E. Sievers, Fairborn, Ohio

[73] Assignee: The United States of America as represented by the Secretary of the Air Force, Washington, D.C.

[21] Appl. No.: 439,665

[22] Filed: Feb. 4, 1974

Related U.S. Application Data

[62] Division of Ser. No. 273,003, Jul. 18, 1973, Pat. No. 3,846,333, which is a division of Ser. No. 183,488, Sep. 24, 1971, Pat. No. 3,700,410.

[51] Int. Cl.$^2$ ............................................. C07F 5/00
[52] U.S. Cl. .............................. 260/429.2; 23/230 M
[58] Field of Search ..................................... 260/429.2

[56] References Cited

U.S. PATENT DOCUMENTS

| 3,558,440 | 1/1971 | Harris et al. ................. 260/429.2 X |
| 3,846,333 | 11/1974 | Sievers ........................ 260/429.2 X |

*Primary Examiner*—Leland A. Sebastian
*Attorney, Agent, or Firm*—Joseph E. Rusz; Cedric H. Kuhn

[57] ABSTRACT

A lanthanide chelate of a fluorinated ligand is used as a nuclear magnetic resonance shift reagent for spectral simplification and clarification. Since the use of the shift reagents of this invention facilitates compound identification and increases the scope of the applicability of nuclear magnetic resonance spectroscopy, the present invention is particularly useful in detecting and analyzing compounds which are or may be pollutants.

11 Claims, 4 Drawing Figures

LANTHANIDE CHELATE OF A FLUORINATED LIGAND

This application is a division of pending application Ser. No. 273,003 filed on July 18, 1973, which was a division of Ser. No. 183,488 filed on Sept. 24, 1971, and now issued as U.S. Pat Nos. 3,846,333 and 3,700,410, respectively.

FIELD OF THE INVENTION

This invention relates to the spectral analysis of organic compounds having a conor group by nuclear magnetic resonance (NMR). In one aspect, it relates to a composition which, when added to a compound to be identified by NMR, facilitates the interpretation of the compound's spectrum. In another aspect, it relates to a composition which, when analyzed by NMR, has a spectrum which is readily interpreted.

BACKGROUND OF THE INVENTION

NMR spectroscopy has been used for many years in the identification of compounds by comparing the spectra of known compounds with those of the compounds to be analyzed. The techniques employed in this method of spectral analysis are described in the literature, and NMR spectrometers are commercially available. For a discussion of the theory of nuclear magnetic resonance and a decription of the basic components of an NMR spectrometer and its operation, reference may be made to Van Nostrand's Scientific Encyclopedia, 4th Ed., D. Van Nostrand Company, Inc., Princeton, New Jersey. Briefly, in the operaton of a spectrometer, a tube containing a sample to be analyzed is positioned between the pole faces of a direct current electromagnet whose gap can be varied. An oscillating radio frequency field is imposed at right angles to the magnetic field. A separate radio frequency coil in the form of a few turns of wire wound tightly around the sample tube serves as the receiver coil to pick up the resonant signal from the sample. When nuclear transitions are induced, energy is absorbed from the receiver coil, causing the voltage across the receiver coil to drop. After this voltage change is amplified and detected, the resulting direct current voltage is placed on an oscilloscope. The NMR spectrum, a pattern of intensity as a function of frequency, is thereby produced. An interpretation of the spectrum makes it possible to determine the nuclei present in molecules and their relations to the remainder of the molecule.

Since the beginning of NMR spectroscopy in the late 1940's, the effects of paramagnetism on nuclear magnetic resonances have been the subject of considerable study. The object of the study has been to provide means to simplify and clarify the NMR spectrum, thereby rendering compound identification more certain as well as increasing the scope of the applicability of NMR spectroscopy. The results of the study have been the development of so-called shift reagents which, when added to a sample of a compound subjected to NMR, will cause frequency shifts that desirably will result in a high resolution spectrum without objectionable peak broadening. Although large frequency shifts caused by several paramagnetic chelates have been observed, up to the present time much of the work has revolved around the question of which metal will permit the observation of such high resolution spectra of its complexes. It has been reported [J. Amer. Chem. Soc., 91, 5160 (1969)] that the dipyridine adduct of tris(2,2,6,6-tetramethyl-3,5-heptanedionato) europium-(III) produces relatively large concentration-dependent paramagnetic shifts in cholesterol monohydrate without serious peak broadening. Subsequently, it was reported [(Chem. Commun., 422 (1970)] that the coordinating effectiveness of the europium was significantly improved by elimination of the pyridine using the unsolvated europium chelate of 2,2,6,6-tetramethyl-3,5-heptanedione[Eu(thd)$_3$].

While the above-mentioned chelates are useful as shift reagents for specific classes of compounds, their effectiveness is drastically reduced when used with weak Lewis bases. Moreover, the solubility of the thd chelates is relatively low in nonalcoholic solutions. As a result free ligand and complexed ligand are present, a condition that limits the spectral shifts obtainable.

It is an object of this invention, therefore, to provide superior paramagnetic shift reagents for nuclear magnetic resonance spectral clarification.

Another object of the invention is to provide shift reagents that can be effectively used with organic compounds having a donor group, such as weak Lewis bases.

A further object of the invention is to provide shift reagents that are highly soluble in nonalcoholic solutions.

Still another object of the invention is to provide an improved method of spectral analysis of an organic compound having a donor group by nuclear magnetic resonance.

A still further object of the invention is to provide a composition which, when added to a compound, greatly simplifies and clarifies its spectrum.

Yet another object of the invention is to provide a composition which, when subjected to NMR, has a spectrum that can be readily interpreted.

Other and further objects and advantages of the invention will become apparent to those skilled in the art upon consideration of the accompanying disclosure and the drawing, in which.

SUMMARY OF THE INVENTION

Figure 1:
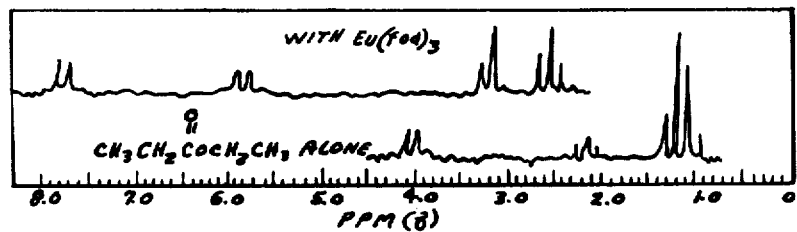
FIG. 1 shows the spectra of ethyl propionate without a shift reagent and with a shift reagent of this invention.

The present invention resides, in the discovery that lanthanide chelates of fluorinated ligands, when used as paramagnetic shift reagents, result in easily interpreted high resolution spectra of their complexes with organic compounds having a donor group. The lanthanide chelates that can be used in the practice of the present invention can be represented by the following structural formula:

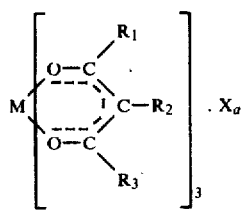

wherein M is a rare earth element of the lanthanide series; $R_1$, $R_2$ and $R_3$ are individually selected from the group consisting of hyddrogen, deuterium, alkyl and fluoroalkyl, at least one of the $R_1$, $R_2$ and $R_3$ groups being fluoroalkyl; or $R_1$ and $R_2$ together are d-camphor and $R_3$ is fluoroalkyl; X is an organic compound contaning a donor group; and a is a numeral from zero to 4, inclusive. The alkyl and fluoroalkyl groups contain from 1 to 10, inclusive, preferably from 1 to 4, inclusive, carbon atoms.

As indicated in the foregoing paragraph, the letter "X" represents an organic compound containing a donor group, which combines in molecular form with the lanthanide chelate. Examples of such compounds include water, methyl alcohol, acetone, dimethylformamide, dimethoxypropane, and the like.

The lanthanide chelates defined by the above formula that are operable in the practice of the present invention are those in which the letter "M" represents the paramagnetic trivalent rare earth ions. These ions and their symbols in the order of their atomic numbers are cerium (Ce), praseodymium (Pr), neodymium (Nd), samarium (Sm), europium (Eu), gadolinium (Gd), terbium (Tb), dysposium (Dy), holmium (Ho), erbium (Er), thulium (Tm), and ytterbium (Yb). Of the chelates it is preferred to utilize those according to the above formula in which M is Eu or Pr.

Examples of lanthanide chelates as defined by the foregoing formula include tris (1,1,1,2,2,3,3-heptafluoro-7,7-dimethyloctane-4,6-dionato)europium(III) [Eu(fod)$_3$]; tris(1,1,1,2,2,3,3-heptafluoro-7,7-dimethyloctane-4,6-dionato)praseodymium(III) [Pr(fod)$_3$]-tris(1,1,1,2,2,3,3,7,7,7-decafluoro-4,6-heptanedionato)europium(III)dihydrate; tris(1,1,1,2,2,3,3,7,7,7-decafluoro-4,6-heptanedionato)praseodymium(III)-dihydrate; tris(1,1,1,2,2,3,3,7,7,7-decafluoro-4,6-heptanedionato)ytterbium(III); tris(1,1,1,2,2,3,3,3-heptafluoro-7,7-dimethyloctane-4,6-dionato)ytterbium(III); dimethylformamide adduct of tris(1,1,1,5,5,5,-hexafluoro-2,4-pentanedionato) europium(III); perdeuterated tris(1,1,1,2,2,3,3-heptafluoro-7,7-dimethyloctane-4,6-dionato)europium(III); perdeuterated tris(1,1,1,2,2,3,3-heptafluoro-7,7-dimethyloctane-4,6-dionato)praseodymium(III); tris(trifluoroacetyl-d-camphorato)europium(III); and the like.

The lanthanide chelates represented by the above formula (except for those in which $R_1$ and $R_2$ together are d-camphor) and methods for their synthesis are described in the literature. In this regard attention is directed to Inorganic Chemistry, 6, 1105 (1967) and Inorganic Chemistry, 10, 498 (1971), which are incorporated herein by reference. The chelates in which $R_1$ and $R_2$ together are d-camphor and $R_3$ is a fluoroalkyl, can be synthesized by preparing an alcohol solution of trifuloroacetyl-d-camphor [H(facam)] and adding this solution to an aqueous solution of a chloride of one of the aforementioned rare earth elements. For example, in the synthesis of tris(trifluoroacetyl-d-camphorato)-praseodymium(III) [Pr(facam)$_3$], a first solution is prepared by stirring 15 millimols (3.70 grams) of H(facam) into 100 milliliters of a 50 percent alcohol solution. A 10 percent ammonium hydroxide solution is slowly added until all of the H(facam) is dissolved. A second solution is prepared by adding 5 milliliters of a 1 molar aqueous solution of praseodymium chloride (5 millimols) to 20 milliliters of alcohol. The first solution is then added dropwise to the second solution while stirring vigorously. The precipitate that forms is stirred in the mother liquor for an additional time, e.g., for about one hour, after all of the first solution has been added. The mixture is then filtered and the precipitate is washed with 100 milliliters of a 50 percent alcohol solution. After the precipitate is air dried overnight, it is recovered and the product obtained is determined by analysis to be Pr(facam)$_3$.

In one embodiment the present invention resides in an improvement in the spectral analysis by nuclear magnetic resonance of an organic compound having a donor group. The improvement comprises the step of mixing with the organic compound to be analyzed a shift reagent which is a lanthanide chelate of a fluorinated ligand as defined hereinabove, the shift reagent and the organic compound being in solution in a common solvent. The shift reagent can be in solution in the solvent in which case the compound to be analyzed is added to the solution. Alternatively, the compound to be analyzed can be in solution, and in this case the shift reagent is added to the solution. Furthermore, the shift reagent and the compound to be analyzed can be in separate solutions in which event the two solutions are mixed.

Conditions for resonance are expressed in terms of a difference (chemical shift) between the field necessary for resonance in the sample and in an arbitrarily chosen reference material. Thus, samples to be subjected to nuclear magnetic resonance conventionally contain a reference material having only a single resonance line, which serves to locate the resonant frequency of a sample in a magnetic field. Examples of suitable reference compounds include tetramethyl silane (TMS), chloroform, cyclohexane and benzene. The reference material can be added to the compound to be analyzed, to the shift reagent or to the solution or solutions containing these materials.

In general, solvents suitable for use are compounds in which both the shift reagent and the compounds to be analyzed are soluble. Also, the compounds useful as solvents are those that either do not absorb, or if they do absorb, the absorption occurs in a region that does not interfere with the sample spectrum. Examples of suitable solvents include carbon tetrachloride, chloroform, deuterated methylene chloride, benzene, deuterated benzene, and the like.

In another embodiment, the invention resides in a composition which comprises a solution of a lanthanide chelate of a fluorinated ligand, as defined above, in a solvent therefor. Generally, the solution contains about 0.01 to 0.5 mol of the chelate per 1000 milliliters of the solvent. The composition may also contain a reference compound, the amount usually being in the range of about 0.1 to 1 weight percent, based on the weight of the solution.

In still another embodiment, the invention resides in an adduct of a lanthanide chelate of a fluorinated ligand, as defined above, and an organic compound having a donor group. The adduct is in solution and is formed when the chelate and the organic compound are mixed in the solvent prior to subjecting the sample to NMR. The mol ratio of chelate to organic compound to achieve complete coordination will vary with the particular chelate and organic compound employed. However, this ratio can be readily determined by one skilled in the art by observing the point where further addition of the chelate causes no further spectral shift. It is to be understood, however, that the adduct is present in solution prior to the addition of the amount necessary to cause a maximum spectral shift.

In general, the paramagnetic shift reagents of this invention can be used in the spectral analysis by nuclear magnetic resonance of organic compounds having a donor group. Classes of such compounds include ethers, esters, ketones, alcohols, amines, acids, amino acids, oximes, sulfides, sulfoxides, nitriles and amides as well as various natural products and compounds that can be classified as pollutants. Specific examples of compounds of the aforementioned classes include the following: ethyl ether, di-n-butyl ether, methyl n-propyl ether, methyl tert-propyl ether, n-propyl ether, tert-butyl ether, 1-chloroethyl ethyl ether, vinyl ether, vinyl methyl ether, vinyl ethyl ether, allyl ether, ethynyl ethyl ether, benzyl methyl ether, benzyl ethyl ether; 2-ethylhexyl acetate, hexyl acetate, isoamyl acetate, ethyl propionate, ethyl acetate, butyl acetate, cellulose acetate, isopropyl acetate, dibutyl phthalate, di-n-octyl phthalate, diethylene glycol monolaurate, 1,2-propylene glycol monolaurate, butyl oleate, butyl stearate, benzyl acetate, benzyl benzoate, benzyl propionate, methyl benzoate, methyl salicylate, methyl formate, triethyl orthoformate, ethyl acetoacetate; methyl n-propyl ketone, acetone, methyl ethyl ketone, diethyl ketone, diisobutyl ketone, methyl vinyl ketone, methyl propenyl ketone, acetol, acetoin, acetopropanol, chloroacetone, chloropentanone, cyclohexanone, isophorone, acetophenone, benzophenone, acrylophenone, benzoin, xanthone; ethyl alcohol, isopropyl alcohol, methylethyl carbinol, pentanol, tertiary butyl carbinol, n-hexyl alcohol, n-octyl alcohol, n-decyl alcohol, lauryl alcohol, cetyl alcohol, eicosyl alcohol, cyclohexanol, allyl alcohol, propargyl alcohol, ethylphenyl alcohol, benzyl alcohol, menthol, glycerol, erythritol; methylamine, isopropylamine, n-butylamine, allylamine, dimethylamine, diisopropylamine, di-n-amylamine, methylethylamine, trimethylamine, tri-n-butylamine, triisoamylamine, ethylenediamine, hexamethylenediamine, cyclohexylamine, aniline, α-naphthylamine, o-chloroaniline, m-toluidine, diphenylamine, o-phenyldiamine, p-toluenediamine, benzidine, 2-aminopyridine, 2-aminothiazole; formic, acetic, butyric, acrylic, methacrylic, propiolic, valeric, caproic, caprylic, lauic, palmitic, stearic, oleic, lanoleic, oxalic, malonic, succinic, adipic, sebacic, maleic, fumaric, acetylenedicarboxylic, aconitic, glycolic, lactic, malic, citric, glyoxylic, acetoacetic, bromoacetic, and thioglycolic acids; alanine, arginine, citrulline, glutamic acid, glycine, hastidine, lysine, methionine, proline, tyrosine, valine, isoleucine, phenylalanine, ornithine, proline; acetaldoxime, propionaldoxime, acrylaldoxime, choral oxime, α-benzadoxime, β-benzadoxime, phenylacetaldoxime, o-tolualdoxime, m-tolualdoxime, p-tolualdoxime, glyoxime, acetoxime, diisopropyl ketoxime, cyclopentanone oxime, α-d-carvoxime, β-d-carvoxime, acetophenone oxime, dimethylglyoxime, quinone dioxime; dimethyl sulfide, methylene sulfide, diethyl sulfide, divinyl sulfide, diallyl sulfide, dichloro ethyl sulfide, dibenzyl sulfide, diphenyl sulfide, carbonyl sulfide, acetyl disulfide, benzoyl disulfide, allyl trisulfide; phenyl sulfoxide, dimethyl sulfoxide, dibenzyl sulfoxide, diphenyl sulfoxide; acetonitrile, butyronitrile, isobutyronitrile, acrylo nitrile, succinonitrile, dodecanedinitrile, cyclohexanecarbonitrile, benzonitrile, phenylacetonitrile; formamide, acetamide, stearamide, acetanilide, acetoacetanilide, benzanilide, urea, thiourea, cyanamide, sulfamide, trifluoroacetyl amides derived from amino acids (e.g., trifluoroacetylalanine); and the like. Examples of natural products include camphor, lanosterol, lanolin, testosterone, DDE (metabolite of DDT), androsterone, cholesterol, and etiocholanoline. Examples of pollutants that can be identified by the practice of the present invention include peroxyacylnitrate, acetaldehyde, benzaldehyde, formaldehyde, isoamyl alcohol, ethyl acetate, n-propanol, isopropanol, heptachlor epoxide, dieldrin, and butyric acid.

The shift reagents of this invention are greatly superior to the prior art reagents, e.g., tris(2,2,6,6-tetramethyl-3,5-heptanedionato)europium(III) [Eu(thd)$_3$], when used with weak Lewis bases. This superiority is based upon the discovery that the lanthanide chelates of fluorinated ligands as defined above are more highly soluble in nonalcoholic solutions and possess a higher Lewis acidity. Thus, it has been found that substitution of fluorocarbon moieties in β-diketonate ligands increases the solubility of the metal complex while the electron-withdrawing fluorines increase the residual acidity of the cation, making it a better coordination site for weak donors. Because of these properties they are effective in forming adducts with organic compounds containing a donor group. And by forming adducts, the shift reagents cause the NMR spectra to be shifted greatly relative to the spectra of the organic species alone. The resulting spectra are thereby more easily interpreted than the cluttered and often indecipherable spectra of the organic compounds along.

A better understanding of the invention can be obtained from a consideration of the following examples which are not intended, however, to be unduly limitative of the invention.

EXAMPLE I

Two experiments were conducted in which NMR spectra were obtained at 60 MHz with carbon tetrachloride solutions containing 0.1 m mol of ethyl propionate. A Varian HA-60-IL spectrometer was used and tetramethyl silane (TMS) was employed as the internal reference. In the first experiment a shift reagent was not used while in the second experiment Eu(fod)$_3$ was employed as a shift reagent. The sample for the first experiment was prepared by adding the TMS and 10 mg of ethyl propionate to 0.5 ml of CCl$_4$ in the sample tube. In the second experiment, the sample was prepared in the same manner except that 25 mg of Eu(fod)$_3$ (2.5×10$^{-5}$ mol) was added to the solution of ethyl propionate in CCl$_4$.

The results obtained in the two experiments are shown in FIG. 1 of the drawing. The lower trace shows the spectrum of ethyl propionate alone while the upper trace shows the spectrum of ethyl propionate with added Eu(fod)$_3$. As seen from a comparison of the two spectra, the presence of a shift reagent of this invention caused the NMR spectrum to be shifted (down-field) greatly relative to the NMR spectrum of ethyl propionate alone. As a result the spectrum with Eu(fod)$_3$ is spread out, making it much easier to interpret than the spectrum of ethyl propionate alone.

EXAMPLE II

A series of experiments was conducted in which NMR spectra were obtained at 60 MHz with $CCl_4$ solutions containing 0.1 m mol of di-n-butyl ether. The spectrometer used was the same as the one mentioned in Example I and TMS was employed as the reference material. In one of the experiments a shift reagent was not used while in the other experiments varying amounts (10, 25, 50 and 75 mg) of $Eu(fod)_3$ were added to the solution of the ether in $CCl_4$. The samples were prepared in the same manner as described in Example I.

Figure 2:
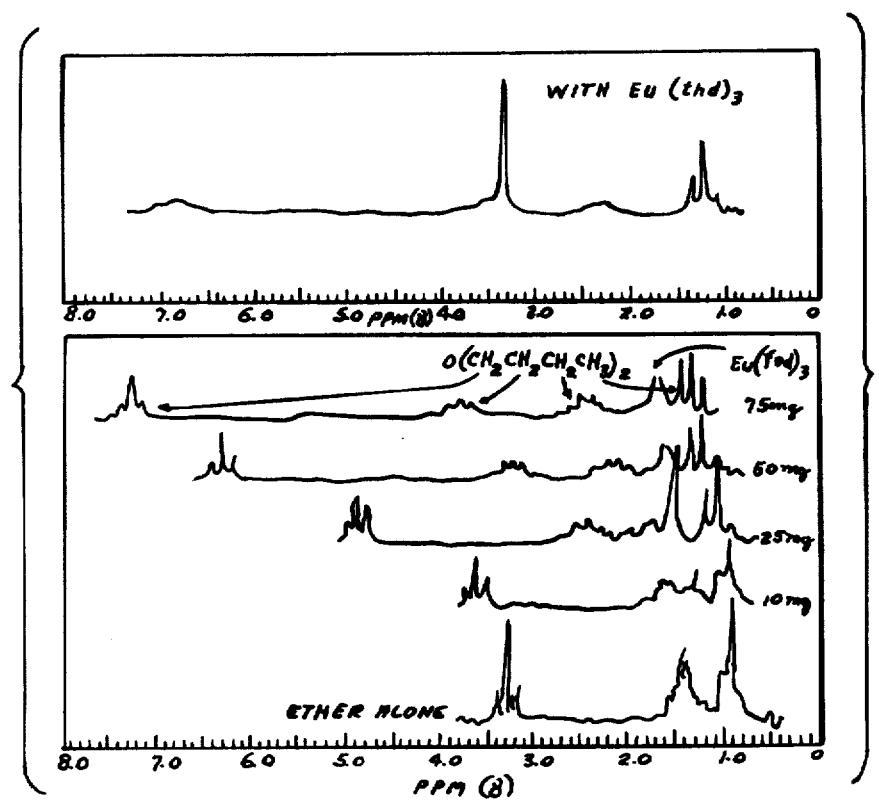
FIG. 2 shows the spectra of di-n-butyl ether with Eu(thd)$_3$, with varying amounts of a shift reagent of this invention, and without any shift reagent.

The results obtained in the series of experiments are shown in the lower portion of FIG. 2. In the lower portion of the figure, the lower trace shows the spectrum of the ether alone, while the upper four traces in the same portion of the figure show the spectra of the ether with added amounts of $Eu(fod)_3$. The amount of added $Eu(fod)_3$ is shown to the right of the trace of the spectrum of the sample containing that amount. As seen from a comparison of the five spectra, the presence of $Eu(fod)_3$ caused the NMR spectra to be shifted relative to the NMR spectrum of ether alone. Also, increasing the amount of added $Eu(fod)_3$ resulted in the attainment of progressively larger induced shifts. As shown by the top trace, addition of 75 mg of $Eu(fod)_3$ resulted in a greatly simplified spectrum that could be easily interpreted to identify the ether.

An esperiment was conducted in which the NMR spectra was obtained with a $CCl_4$ solution of di-n-butyl ether, following the same procedure as described above except for the differences noted hereinafter. Thus, $Eu(thd)_3$ was used as the shift reagent instead of $Eu(fod)_3$. Also, upon adding $Eu(thd)_3$ to the ether solution, the latter was heated in order to dissolve as much of the Eu complex as possible. Therefore, the shifts induced in the ether were the maximum obtainable with $Eu(thd)_3$. The spectrum obtained is shown in the upper part of FIG. 2. From a consideration of this spectrum and those obtained with $Eu(fod)_3$, it is seen that $Eu(thd)_3$ is by comparison ineffective as a shift reagent. The superiority of $Eu(fod)_3$ as a shift reagent can be attributed to its higher solubility and its greater Lewis acidity.

EXAMPLE III

Figure 3:
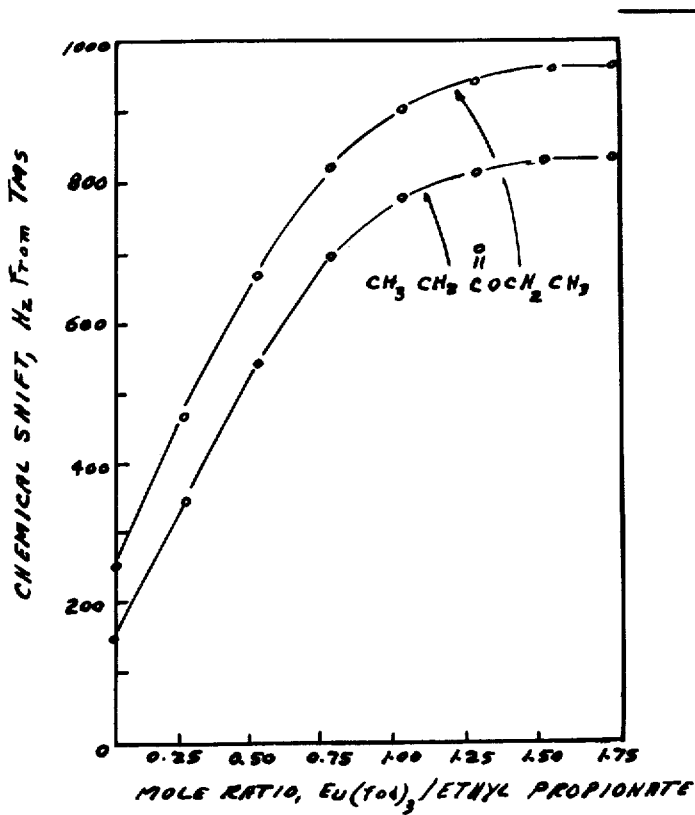
FIG. 3 is a graph that shows induced contact shifts of methylene resonances of ethyl propionate as a function of added shift reagent.

A series of experiments was conducted in which the NMR spectra were obtained with solutions containing 10 mg of ethyl propionate in 0.5 ml of $CCl_4$. TMS was used as the internal reference. A spectrum was obtained for the ester alone, and spectra were also obtained for the ester after adding $Eu(fod)_3$ in increments of 25 mg. The induced contact shifts of the methylene resonances of the ester as a function of $Eu(fod)_3$ were measured in hertz from TMS (internal). The results were plotted and the graphs obtained are shown in FIG. 3. The induced contact shifts of methyl resonances of the ester as a function of $Eu(fod)_3$ were also measured in hertz from TMS (internal). The results obtained are shown graphically in FIG. 4.

Figure 4:
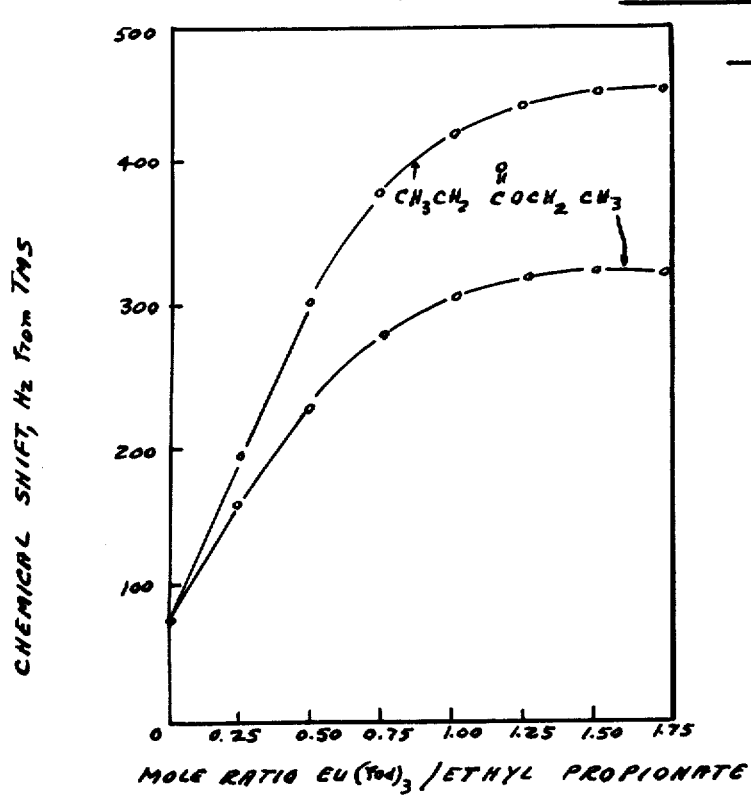
FIG. 4 is a graph that shows induced contact shifts of methyl resonances of ethyl propionate as a function of added shift reagent.

The graphs of FIGS. 3 and 4 demonstrate that at lower concentrations there is an essentially linear dependence of the paramagnetic shifts on added $Eu(fod)_3$. However, in the case of both methylene and methyl groups, a point was reached where further additions of the shift reagent caused no further spectral shifts. These data indicate that the shift is due to bonding of the organic donor groups with the coordinatively unsaturated europium chelate and that the spectrum in which there are no further spectral shifts is essentially that of a coordinated ligand rather than that of the average of the free ligand and complexed ligand.

Furthermore, because the shift reagents of this invention are highly soluble, it is possible to use rare earth ion to organic donor ratios that are high enough to permit the assignment of a constant value to a given compound. This is of great assistance in compound identification, a technique that was not possible with prior art shift reagents because of their low solubility. To establish with certainty the identity of compounds with similar spectra, it is only necessary to add a large excess of the shift reagent, e.g., $Eu(fod)_3$, and observe the spectrum of the resulting complexed ligands. The formation constant can be determined from data of the type shown in FIGS. 3 and 4. The large molar ratio of $Eu(fod)_3$ to organic compound needed to reach the saturation point as shown on the graphs is indicative of the low basicity of the organic compounds and the extreme solubility of the fod complex. For example, in the case of ether, 2.0 mol equivalents of the chelate was required to achieve complete coordination of the ether. This represents a solubility of over 200 mg of the europium complex in a 0.5 ml $CCl_4$ solution of the ether. An important function of the fod ligand is, therefore, to impart extremely high solubility to the resulting complex, thereby making it possible to attain larger induced shifts.

EXAMPLE IV

An experiment was conducted in which $Eu(fod)_3$ was added to a solution of trifuloroacetyl-d-alanine in $CCl_4$. The procedure followed was essentially the same as that described in Example I. A comparison of the spectra with and without the $Eu(fod)_3$ indicated that the addition of the shift reagent resulted in the methyl resonance being shifted downfield by 0.66 ppm($\delta$).

EXAMPLE V

Experiments were conducted in which $Pr(fod)_3$ and tris(1,1,1,2,2,3,3,7,7,7-decafluoro-4,6-heptanedianato) praseodymium (III) dihydrate $[Pr(dfhd)_3.(H_2O)_2]$ were separately added to a solution of di-n-butyl ether in $CCl_4$. The procedure followed was essentially the same as that described in Example I. A comparison of the spectra indicated that the resonances of the ether with added $Pr(fod)_3$ or $Pr(dfhd)_2.(H_2O)_2$ were shifted upfield to new positions relative to the resonances of the ether alone.

EXAMPLE VI

Experiments were conducted in which $Eu(fod)_3$ was added to solutions of 2-pentanone in $CCl_4$ and to a solution of hexyl acetate in $CCl_4$. The procedure followed was essentially that of Example I. A comparison of the spectra of 2-pentanone and hexyl acetate with and without the $Eu(fod)_3$ showed that the resonance peaks were all shifted downfield to new values relative to each other. In many cases, peaks that were superimposed in the spectra of the organic compounds alone appeared separately so that they were easier to assign.

EXAMPLE VII

An experiment was conducted in which $Eu(fod)_3$ was added to a mixture of acetone, methyl acetate, cyclohexane and tetramethyl silane (TMS). The NMR spectrum of the mixture was greatly clarified as a result of the addition of the shift reagent. Thus, the cyclohexane peak did not shift relative to the TMS, which was used as a reference. The other peaks on the other hand were all shifted downfield.

The data in the foregoing examples demonstrate that the addition of the shift reagents of this invention to organic compounds containing a donor group result in spectra that are greatly spread out, resulting in the resolution of overlapping peaks. The spectra are thereby clarified so that they can be more easily and accurately interpreted. Because the solubility of the shift reagents in nonalcoholic solutions is much higher than that of the prior art reagents, a shorter time is required in making a spectral analysis and a much wider range of spectra can be clarified.

In the practice of the present invention, a mixture of rare earth shift reagents can be employed as well as a single one. It is preferred to use shift reagents that are prepared from the ligands 1,1,1,2,2,3,3-heptafluoro-7,7-dimethyl-4,6-octanedione [H(fod)]; 1,1,1,2,2,3,3,7,7,7-decafluoro-4,6-heptanedione [H(dfhd)]; and trifluoroacetyl-d-camphor [H(facam)]. The preferred shift reagents derived from these fluorinated ligands are Eu(fod)$_3$, Pr(fod)$_3$, Eu(dfhd)$_3$.(H$_2$O)$_2$, Pr(dfhd)$_3$.(H$_2$O)$_2$, Eu(facam)$_3$, and Pr(facam)$_3$. The deuterated or partially deuterated analogs of these chelates are also particularly desirable for use as shift reagents. However, it is to be understood that other lanthanide chelates of fluorinated ligands, as defined hereinbefore by the structural formula, can be advantageously utilized in the practice of this invention.

As previously indicated, the paramagnetic shift reagents of this invention are applicable to the spectral analysis of organic compounds having a donor group. The wide applicability of the shift reagents results from the use of fluorinated ligands in preparing the rare earth chelates. The presence of electron-withdrawing fluorine increases the residual acidity of the cation of the rare earth chelates, making it a good coordination site even for weak donors. Thus, the paramagnetic shift reagents are outstandingly effective in clarifying the spectra of organic Lewis bases, thereby facilitating their interpretation. A particularly important application of the present invention is in the identification of pollutants. Often the identity of an offending compound is unknown and is present in admixture with other materials. In accordance with the present invention, spectra can be obtained that are spread out and uncluttered by overlapping NMR peaks. As a result it is possible to identify the unknown pollutant in a minimum of time, the initial step to be taken in control of the pollutant.

Another important specific application of the present invention resides in the use of optically active facam chelates, e.g., Eu(facam)$_3$ and Pr(facam)$_3$, as shift reagents to distinguish dextro and levo isomers of various compounds such as amino acid derivatives. Furthermore, the shift reagents of this invention can be employed to clarify the NMR spectra of other nuclei such as $^{13}$C, $^{19}$F, $^{15}$N, and the like.

In view of the foregoing disclosure, improvements and modifications of the invention may be made by those skilled in the art. Such modifications and improvements fall within the spirit and scope of the invention.

I claim:

1. As a composition of matter, a tris(1,1,1,2,2,3,3,7,7,7-decafluoro-4,6-heptanedionato)-lanthanide(III)hydrate.

2. The composition according to claim 1 in which the lanthanide is praseodymium.

3. The composition according to claim 1 in which the lanthanide is ytterbium.

4. The composition according to claim 1 in which the lanthanide is europium.

5. The composition according to claim 1 in which the lanthanide is samarium.

6. The composition according to claim 1 in which the lanthanide is neodymium.

7. Tris(trifluoroacetyl-d-camphorato)europium(III).

8. Tris(trifluoroacetyl-d-camphorato)praseodymium(III).

9. The europium and praseodymium chelates having the general formula:

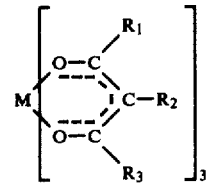

in which R$_1$ and R$_2$ together are d-camphor, R$_3$ is a fluorinated alkyl group having from one to ten carbon atoms and M is europium (III) or praseodymium (III).

10. The chelates as claimed in claim 7 in which the R$_3$ group has from one to four carbon atoms.

11. A lanthanide chelate having the following formula:

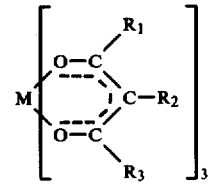

in which M is a rare earth element of the lanthanide series, R$_1$ and R$_2$ together are d-camphor, and R$_3$ is fluoroalkyl.

* * * * *

UNITED STATES PATENT AND TRADEMARK OFFICE
CERTIFICATE OF CORRECTION

PATENT NO. : 4,206,132
DATED : June 3, 1980
INVENTOR(S) : Robert E. Sievers

It is certified that error appears in the above—identified patent and that said Letters Patent is hereby corrected as shown below:

On the front page in item [73] Assignee:
"The United States of America as represented by the Secretary of the Air Force, Washington, D. C."
should be deleted and -- Motion Manufacturing Inc., Detroit, Mich. -- substituted therefor.

Signed and Sealed this

Twenty-eighth Day of October 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,206,132
DATED : June 3, 1980
INVENTOR(S) : Robert E. Sievers

It is certified that error appears in the above-identified patent and that said Letters Patent are hereby corrected as shown below:

On the front page, change the inventor's address in item [75] from "Fairborn, Ohio" to -- Boulder, Colorado --.

On the front page delete:
(73) Assignee: The United States of America as represented by the Secretary of the Air Force This certificate supersedes certificate of correction issued October 28, 1980.

Signed and Sealed this

*Thirty-first* Day of *March 1981*

[SEAL]

*Attest:*

RENE D. TEGTMEYER

*Attesting Officer*    *Acting Commissioner of Patents and Trademarks*